United States Patent [19]

Avery

[11] Patent Number: 4,492,305

[45] Date of Patent: Jan. 8, 1985

[54] PACKAGE FOR COLLECTING CULTURES

[75] Inventor: Carl F. Avery, Overland Park, Kans.

[73] Assignee: Marion Laboratories, Inc., Kansas City, Mo.

[21] Appl. No.: 511,851

[22] Filed: Jul. 8, 1983

[51] Int. Cl.³ .................... B65D 81/22; B65D 85/50; C12B 1/00; C12K 1/10
[52] U.S. Cl. .................................. 206/210; 206/205; 206/361; 435/295
[58] Field of Search ............... 206/210, 209, 361, 205, 206/63.5; 435/295; 215/32

[56] References Cited

U.S. PATENT DOCUMENTS

| | | | |
|---|---|---|---|
| 3,419,172 | 12/1968 | Lee | 215/32 |
| 3,858,739 | 1/1975 | Turner et al. | 215/32 |
| 3,890,204 | 6/1975 | Avery | 195/139 |
| 4,175,008 | 11/1979 | White | 206/209 |

Primary Examiner—William T. Dixson, Jr.
Attorney, Agent, or Firm—Leydig, Voit, Osann, Mayer & Holt, Ltd.

[57] ABSTRACT

A culture collecting swab and a sealed glass ampoule packaged end to end in an envelope and initially are held in an assembled condition by a resiliently yieldable closure member which is carried on the end of the stem of the swab and which includes a cup portion snugly telescoped on one end portion of the ampoule. After a culture has been collected on the tip of the swab, the ampoule is broken open along a score line inside the cup portion of the closure member, the end portion broken off the ampoule being retained in the cup portion. The tip and end of the swab are then inserted into the ampoule through the open end thereof to immerse the tip in a culture-sustaining media and, as an incident to this, a plug portion on the closure member enters and closes the open end of the ampoule.

3 Claims, 6 Drawing Figures

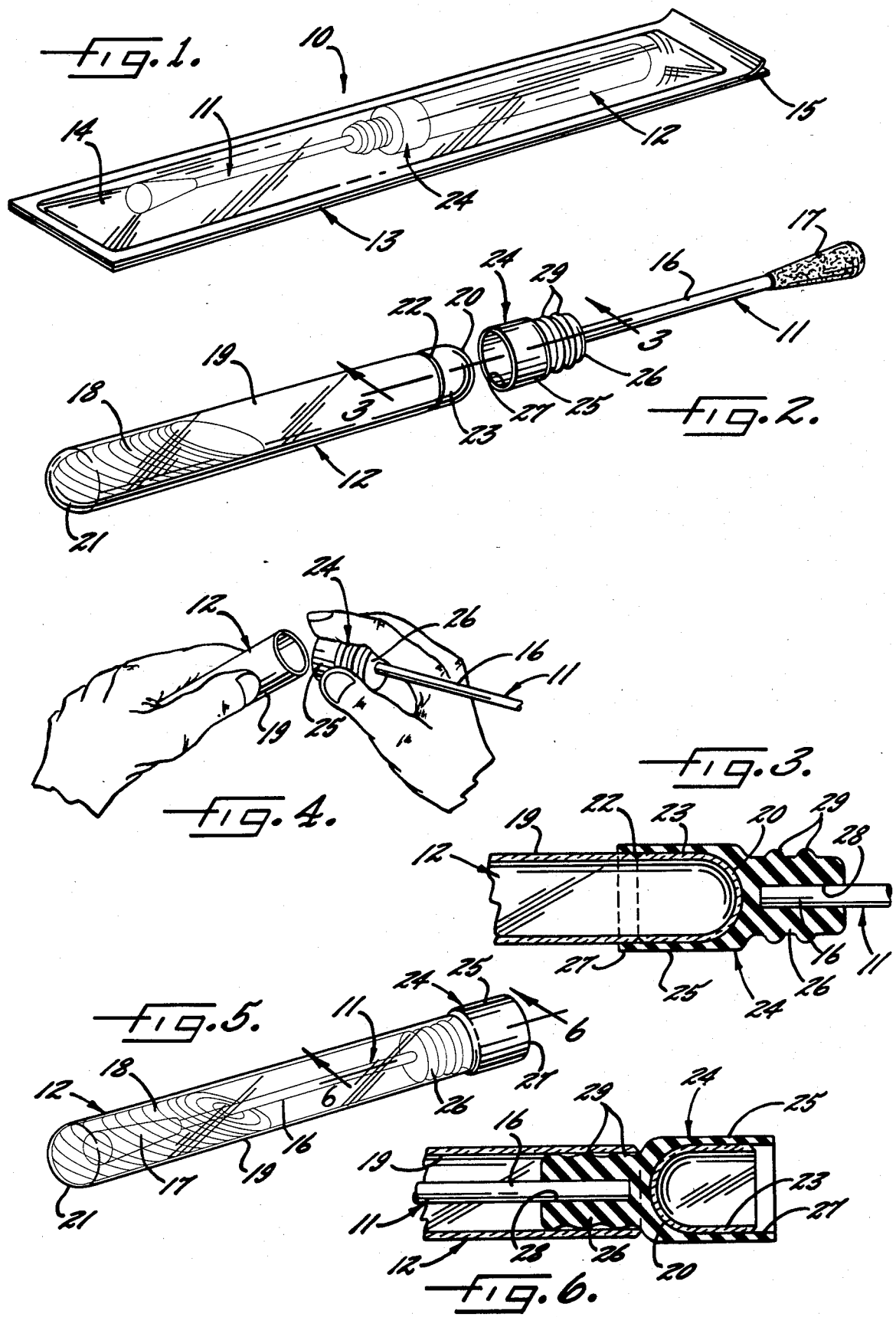

PACKAGE FOR COLLECTING CULTURES

BACKGROUND OF THE INVENTION

This invention relates to devices used by physicians and the like for collecting a culture from a selected area of a patient's body and keeping the culture alive for a period of time until it can be tested. Such devices customarily include an absorbent swab for collecting the culture by swabbing a particular body area and they further include a container having its own supply of a culture-sustaining media. After the culture has been collected, the swab is inserted in the container to place the swab in contact with the media to keep the culture alive until it is ready for testing. The container preferably is a sealed glass ampoule which can be sterilized easily and effectively and which does not react with either the culture-sustaining media or the culture.

In Avery U.S. Pat. No. 3,890,204, such a device is shown as a package and includes an elongated glass ampoule and a separate swab comprising a swabbing tip carried on one end of a stem. Near one end, the ampoule is scored circumferentially so that the end portion may be broken off to permit the stem to be inserted in the ampoule through the open end and to immerse the tip in the culture-sustaining media. A closure member is carried by the other end of the stem and, as an incident to inserting the stem in the ampoule, this member closes the open end of the ampoule.

SUMMARY OF THE INVENTION

The general object of the invention is to provide a new and improved culture collecting package which incorporates the basic features of the Avery patent and which, at the same time, protects the user from being cut as the ampoule is broken at the score line and is also comparatively simply and inexpensive to manufacture.

A more detailed object is to achieve the foregoing by providing a novel closure member which, in one orientation of the swab relative to the ampoule, covers the score line while the end portion of the ampoule is broken off and, in another orientation, plugs the open end of the ampoule when the stem of the swab is inserted in the ampoule.

A more detailed object is to make the closure member of a resiliently yieldable material and to form one portion of the member as a cup which telescopes snugly on the end portion to be broken off and another portion of the member as a plug which fits snugly into the open end of the ampoule as the swab is inserted in the ampoule.

The invention also resides in the particular construction of the closure member and in its coaction with the ampoule.

BRIEF DESCRIPTION OF THE DRAWINGS

FIG. 1 is a perspective view of a culture collecting package embodying the present invention.

FIG. 2 is an exploded perspective view of the ampoule and the swab.

FIG. 3 is an enlarged fragmentary sectional view taken along the line 3—3 in FIG. 2.

FIG. 4 is a perspective view illustrating the manner in which the end portion of the ampoule is broken off.

FIG. 5 is a perspective view showing the swab inserted in the ampoule.

FIG. 6 is an enlarged fragmentary sectional view taken along the line 6—6 in FIG. 5.

DETAILED DESCRIPTION OF THE PREFERRED EMBODIMENT

As shown in the drawings for purposes of illustration, the invention is embodied in a package 10 whose components are used for collecting a bacterial specimen or culture from a patient's body and for maintaining the culture in a live condition until such time as it can be tested. The package includes a swab 11 and an ampoule 12 which initially are disposed within a substantially flat envelope 13. The latter comprises a flexible transparent blister 14 which is sealed to a peel-away backing 15. After the swab and the ampoule have been sealed in the envelope, the envelope may be processed in order to sterilize the swab and the outside of the ampoule. The swab and the ampoule may be removed from the envelope by peeling away an end portion of the backing 15 and taking the swab and the ampoule out through the open end of the envelope.

The swab 11 comprises an elongated stem 16 made of plastic and having an absorbent swabbing tip 17 of a material such as cotton on one end thereof. After a culture has been collected on the tip, it is necessary to place the tip in contact with a culture-sustaining media 18 in order to keep the culture in a live condition until it reaches a laboratory for testing. The culture originally is sealed within the ampoule 12 which advantageously is made of glass and which serves as a container for the swab 11 after the culture has been collected.

As shown in FIG. 2, the ampoule 12 is of one-piece construction and includes an elongated tubular body 19 having a circular cross section and having ends which are defined by generally hemispherical domes 20 and 21. The culture-sustaining media 18 is disposed normally within one end portion of the ampoule adjacent the dome 21 and, in this instance, is shown as being a liquid such as modified Stuart's transport media. The media can, however, be a solid substance such an agar slant which may be located in the end portion of the ampoule either with or without a charcoal filtering substance or other filtering agent. Some cultures can survive only in an oxygen-free atmosphere and thus, in some instances, the ampoule also will be filled with a non-oxidizing and preferably heavier-than-air gas such as nitrogen.

The ampoule 12 is opened to permit the swabbing tip 17 to be placed in contact with the media 18 after the culture has been collected on the tip. For this purpose, a circumferentially extending score line 22 (FIGS. 2 and 3) is inscribed on the outside of the ampoule body 19 a short distance beneath the dome 20, the score line preferably extending completely around the body. Thus, the end portion 23 of the ampoule at the dome 20 may be snapped cleanly away from the ampoule body at the break point defined by the score line 22. The swab stem 16 is inserted into the body to place the tip 17 in contact with the media 18 as shown in FIG. 5. As the stem is inserted into the ampoule body, the open end of the body is closed by a closure member 24 which is carried by the stem at the end opposite the tip.

The present invention contemplates the provision of a new and improved package 10 which protects the user against being cut by the glass at the area of the score line 22 and which, at the same time, is comparatively simple and inexpensive to manufacture. To this end, the package includes a novel closure member 24 which, in one orientation of the stem 16 relative to the ampoule 12, covers the score line 22 as the end portion 23 is broken away and, in another orientation, plugs the open end of the ampoule when the stem 16 is inserted in the ampoule to protect a culture on the swabbing tip 17. Thus, the member 24 is made of a resiliently yieldable material such as molded rubber and includes a cup portion 25 which opens longitudinally away from the stem and which may be telescoped snugly over the end portion 23 and remain there as the latter is broken away from the body 19. Extending along the stem toward the swabbing tip is a plug portion 26 of the closure member and this portion is sized to fit snugly in the body 19 and close the open end of the latter when the stem and the tip are inserted into the body.

Herein, the closure member 24 is molded as a single integral part and the inside diameter of the skirt 27 of the cup portion 25 is slightly smaller than the outside diameter of the ampoule body 19. The skirt is stretched to fit snugly over the end portion 23 and the skirt is somewhat longer than the distance from the score line 22 to the adjacent end of the ampoule. Thus, with the cup portion 25 in place on the ampoule, the user may grasp the body 19 in one hand and the cup portion in the other hand and, because of the flexible nature of the cup portion, the user than may break the end portion 23 away as shown in FIG. 4. During such breaking, the skirt 27 protects the user from the score line edges on both the body 19 and the end portion 23 and, in addition, the severed end portion is retained in the cup portion as illustrated in FIG. 6.

The plug portion 26 of the closure member 24 projects axially away from the cup portion 25 and is formed with a central bore 28 slightly smaller in diameter than the stem 16 so that the latter is received tightly in the bore to mount the closure member on the stem. The diameter of the plug portion is somewhat larger than the inside diameter of the ampoule body 19 so that the plug portion is compressed and forms a good closure when it is pushed into the open end of the body as the stem and the tip 17 are inserted into the body as shown in FIG. 6. Preferably, one or more annular ribs 29 are formed around the periphery of the plug portion. The ribs compress against the inside of the body to enhance the closure and, also, the ribs provide a better grip for the user's fingers as when the end portion 23 is being broken off.

Preferably, the ampoule 12 and the swab 11 are packaged in the envelope 13 in the assembled condition with the cup portion 25 of the closure member 24 telescoped on the end portion 23 of the ampoule body 19 in the manner illustrated in FIG. 1. When removed from the envelope, this assembly is used to obtain a culture, the ampoule serving as a handle for the stem and the ribs 29 providing a grip for the user's fingers. Next, the body 19 is gripped in one hand and the end portion 23 is gripped through the skirt 27 in the other hand and the end portion is broken off. With the end portion of the ampoule still retained in the cup portion 25, the swab 11 is turned end for end and is inserted in the ampoule body to immerse the swabbing tip 17 in the culture-sustaining media 18. As an incident to this, the plug portion 26 enters the open end of the body 19, is compressed and tightly closes the ampoule body to preserve the culture until it can be tested.

I claim:

1. A culture collecting package having, in combination, a sealed one-piece ampoule made of glass, said ampoule having an elongated tubular body of circular cross section and having first and second closed ends, a culture-sustaining media contained within said ampoule, a circumferentially extending score line formed in said body a preselected distance from said first end whereby the end portion of the ampoule at said first end may be broken away from the body along the score line to permit access to said media, a swab comprising an elongated stem and a swabbing tip on one end of said stem, and a unitary closure member made of a resiliently yieldable material and mounted on the other end of said stem, said member including a cup portion opening longitudinally away from said stem and sized to snugly receive the outside of said end portion and to extend beyond said score line whereby said end portion may be broken away from said body while inside the cup portion and thereafter is retained in the cup portion, said member also including a plug portion extending along said stem toward said tip and sized to fit snugly into and close the open end of said body after a culture has been collected on said tip and the latter has been inserted in the ampoule and placed in contact with said media.

2. A culture collecting package as defined in claim 1 in which said plug portion is cylindrical and has at least one annular rib extending around the circumference thereof.

3. A culture collecting package as defined in claim 1 in which said ampoule and said swab are packaged with said end portion of said ampoule received in said cup portion of said closure member.

* * * * *